United States Patent
Alkhatib et al.

(10) Patent No.: US 11,278,401 B2
(45) Date of Patent: Mar. 22, 2022

(54) LEAFLET SUTURING TO COMMISSURE POINTS FOR PROSTHETIC HEART VALVE

(71) Applicant: St. Jude Medical, Cardiology Division, Inc., St. Paul, MN (US)

(72) Inventors: Yousef F. Alkhatib, Edina, MN (US); Peter N. Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 116 days.

(21) Appl. No.: 16/683,516

(22) Filed: Nov. 14, 2019

(65) Prior Publication Data

US 2020/0078169 A1    Mar. 12, 2020

Related U.S. Application Data

(63) Continuation of application No. 15/635,476, filed on Jun. 28, 2017, now Pat. No. 10,512,538, which is a continuation of application No. 13/216,124, filed on Aug. 23, 2011, now Pat. No. 9,717,593.

(60) Provisional application No. 61/438,451, filed on Feb. 1, 2011.

(51) Int. Cl.
*A61F 2/24* (2006.01)
*A61F 2/95* (2013.01)

(52) U.S. Cl.
CPC .......... *A61F 2/2418* (2013.01); *A61F 2/2412* (2013.01); *A61F 2/2427* (2013.01); *A61F 2/2436* (2013.01); *A61F 2/95* (2013.01); *A61F 2/9517* (2020.05); *A61F 2002/9534* (2013.01); *A61F 2220/0075* (2013.01); *A61F 2230/0013* (2013.01); *A61F 2250/0039* (2013.01)

(58) Field of Classification Search
CPC ............................ A61F 2/2412; A61F 2/2418
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,491,986 A | 1/1985 | Gabbay |
| 4,580,568 A | 4/1986 | Gianturco |

(Continued)

FOREIGN PATENT DOCUMENTS

| | | |
|---|---|---|
| AU | 2011202175 B1 | 7/2011 |
| CN | 101953725 A | 1/2011 |

(Continued)

OTHER PUBLICATIONS

International Search Report Application No. PCT/US2011/048963, dated Dec. 15, 2011.

(Continued)

*Primary Examiner* — Suba Ganesan
(74) *Attorney, Agent, or Firm* — Lerner, David, Littenberg, Krumholz & Mentlik, LLP

(57) ABSTRACT

A collapsible prosthetic heart valve includes a collapsible and expandable stent and a collapsible and expandable valve assembly. The stent has a proximal end and a distal end. A plurality of commissure points is disposed on the stent. The valve assembly is disposed within the stent and includes a plurality of leaflets. Each leaflet has a free edge. An end portion of the free edge of each leaflet is folded and sutured to a corresponding one of the plurality of the commissure points.

5 Claims, 10 Drawing Sheets

(56) References Cited

U.S. PATENT DOCUMENTS

| | | | |
|---|---|---|---|
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,078,720 A | 1/1992 | Burton et al. | |
| 5,391,172 A | 2/1995 | Williams et al. | |
| 5,411,552 A | 5/1995 | Andersen et al. | |
| 5,415,664 A | 5/1995 | Pinchuk | |
| 5,456,667 A | 10/1995 | Ham et al. | |
| 5,480,423 A | 1/1996 | Ravenscroft et al. | |
| 5,480,424 A | 1/1996 | Cox | |
| 5,484,444 A | 1/1996 | Braunschweiler et al. | |
| 5,702,418 A | 12/1997 | Ravenscroft | |
| 5,824,041 A | 10/1998 | Lenker et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 5,980,533 A | 11/1999 | Holman | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,269,819 B1 | 8/2001 | Oz et al. | |
| 6,368,348 B1 | 4/2002 | Gabbay | |
| 6,391,050 B1 | 5/2002 | Broome | |
| 6,419,695 B1 | 7/2002 | Gabbay | |
| 6,458,153 B1 | 10/2002 | Bailey et al. | |
| 6,468,299 B2 | 10/2002 | Stack et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,682,559 B2 * | 1/2004 | Myers | A61F 2/2412 623/2.13 |
| 6,685,625 B2 | 2/2004 | Gabbay | |
| 6,719,789 B2 | 4/2004 | Cox | |
| 6,730,118 B2 | 5/2004 | Spenser et al. | |
| 6,736,845 B2 | 5/2004 | Marquez et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,326,236 B2 | 2/2008 | Andreas et al. | |
| 7,329,278 B2 | 2/2008 | Seguin et al. | |
| 7,374,573 B2 | 5/2008 | Gabbay | |
| 7,381,218 B2 | 6/2008 | Schreck | |
| 7,399,315 B2 | 7/2008 | Iobbi | |
| 7,419,501 B2 | 9/2008 | Chiu et al. | |
| 7,452,371 B2 | 11/2008 | Pavcnik et al. | |
| 7,476,244 B2 | 1/2009 | Buzzard et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| 7,993,384 B2 | 8/2011 | Wu et al. | |
| 8,043,353 B2 | 10/2011 | Kaufmann et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 8,313,525 B2 | 11/2012 | Tuval et al. | |
| 8,353,955 B2 | 1/2013 | Styrc et al. | |
| 8,562,663 B2 | 10/2013 | Mearns et al. | |
| 8,568,475 B2 | 10/2013 | Nguyen et al. | |
| 8,652,202 B2 | 2/2014 | Alon et al. | |
| 8,679,174 B2 | 3/2014 | Ottma et al. | |
| 8,778,019 B2 | 7/2014 | Knippel et al. | |
| 8,790,386 B2 | 7/2014 | Dwork | |
| 9,039,759 B2 | 5/2015 | Alkhatib et al. | |
| 2002/0036220 A1 | 3/2002 | Gabbay | |
| 2002/0045936 A1 | 4/2002 | Moe | |
| 2002/0183827 A1 | 12/2002 | Derus et al. | |
| 2003/0023303 A1 | 1/2003 | Palmaz et al. | |
| 2003/0040792 A1 | 2/2003 | Gabbay | |
| 2003/0050694 A1 | 3/2003 | Yang et al. | |
| 2003/0130726 A1 | 7/2003 | Thorpe et al. | |
| 2003/0144725 A1 | 7/2003 | Lombardi | |
| 2004/0039436 A1 | 2/2004 | Spenser et al. | |
| 2004/0049262 A1 | 3/2004 | Obermiller et al. | |
| 2004/0093060 A1 | 5/2004 | Seguin et al. | |
| 2004/0093075 A1 | 5/2004 | Kuehne | |
| 2004/0148009 A1 | 7/2004 | Buzzard et al. | |
| 2004/0186563 A1 | 9/2004 | Lobbi | |
| 2004/0210304 A1 | 10/2004 | Seguin et al. | |
| 2004/0260390 A1 | 12/2004 | Sarac et al. | |
| 2005/0004583 A1 | 1/2005 | Oz et al. | |
| 2005/0049667 A1 | 3/2005 | Arbefeuille et al. | |
| 2005/0080476 A1 | 4/2005 | Gunderson et al. | |
| 2005/0096726 A1 | 5/2005 | Sequin et al. | |
| 2005/0137687 A1 | 6/2005 | Salahieh et al. | |
| 2005/0137688 A1 | 6/2005 | Salahieh et al. | |
| 2005/0137691 A1 | 6/2005 | Salahieh et al. | |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2005/0240254 A1 | 10/2005 | Austin | |
| 2005/0256566 A1 | 11/2005 | Gabbay | |
| 2006/0008497 A1 | 1/2006 | Gabbay | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0282150 A1 | 12/2006 | Olson et al. | |
| 2006/0282157 A1 | 12/2006 | Hill et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0156225 A1 | 7/2007 | George et al. | |

(56) References Cited

U.S. PATENT DOCUMENTS

| | | |
|---|---|---|
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0260301 A1 | 11/2007 | Chuter et al. |
| 2007/0288087 A1 | 12/2007 | Fearnot et al. |
| 2008/0004688 A1 | 1/2008 | Spenser et al. |
| 2008/0004696 A1 | 1/2008 | Vesely |
| 2008/0009940 A1 | 1/2008 | Cribier |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228264 A1 | 9/2008 | Li et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269878 A1 | 10/2008 | Iobbi |
| 2008/0269879 A1 | 10/2008 | Sathe et al. |
| 2009/0112309 A1 | 4/2009 | Jaramillo et al. |
| 2009/0118826 A1 | 5/2009 | Khaghani |
| 2009/0138079 A1 | 5/2009 | Tuval et al. |
| 2009/0157175 A1 | 6/2009 | Benichou |
| 2009/0216312 A1 | 8/2009 | Straubinger et al. |
| 2009/0240320 A1 | 9/2009 | Tuval et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 | 2/2010 | Alon et al. |
| 2010/0082094 A1 | 4/2010 | Quadri et al. |
| 2010/0087907 A1 | 4/2010 | Lattouf |
| 2010/0114305 A1 | 5/2010 | Kang et al. |
| 2010/0121434 A1 | 5/2010 | Paul et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0262231 A1 | 10/2010 | Tuval et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0208298 A1 | 8/2011 | Tuval et al. |
| 2011/0282425 A1 | 11/2011 | Dwork |
| 2011/0288626 A1 | 11/2011 | Straubinger et al. |
| 2011/0295216 A1 | 12/2011 | Miller |
| 2012/0022635 A1 | 1/2012 | Yamashita |
| 2012/0053574 A1 | 3/2012 | Murray, III et al. |
| 2012/0071969 A1 | 3/2012 | Li et al. |
| 2012/0078352 A1 | 3/2012 | Wang et al. |
| 2012/0089223 A1* | 4/2012 | Nguyen ............... A61F 2/2418 623/2.14 |
| 2012/0197391 A1 | 8/2012 | Alkhatib et al. |
| 2012/0310332 A1 | 12/2012 | Murray et al. |
| 2013/0030520 A1 | 1/2013 | Lee et al. |
| 2013/0079869 A1 | 3/2013 | Straubinger et al. |
| 2014/0067050 A1 | 3/2014 | Costello et al. |
| 2014/0135909 A1 | 5/2014 | Carr et al. |

FOREIGN PATENT DOCUMENTS

| | | |
|---|---|---|
| DE | 19857887 A1 | 7/2000 |
| DE | 20000659 U1 | 5/2001 |
| DE | 10121210 A1 | 11/2002 |
| DE | 102005003632 A1 | 8/2006 |
| DE | 202008009610 U1 | 12/2008 |
| EP | 0051451 A2 | 5/1982 |
| EP | 0850607 A1 | 7/1998 |
| EP | 0856300 A1 | 8/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1872743 A1 | 1/2008 |
| EP | 1926455 A2 | 6/2008 |
| EP | 1229865 B1 | 11/2010 |
| FR | 2850008 A1 | 7/2004 |
| FR | 2847800 B1 | 10/2005 |
| JP | 2010523234 | 7/2010 |
| JP | 2010528761 A | 8/2010 |
| JP | 2010540079 A | 12/2010 |
| JP | 2011512922 | 4/2011 |
| WO | 9117720 A1 | 11/1991 |
| WO | 9716133 A1 | 5/1997 |
| WO | 9832412 A2 | 7/1998 |
| WO | 1998029057 A1 | 7/1998 |
| WO | 9913801 A1 | 3/1999 |
| WO | 9930646 A1 | 6/1999 |
| WO | 0044313 A1 | 8/2000 |
| WO | 0069368 A2 | 11/2000 |
| WO | 0119285 A1 | 3/2001 |
| WO | 0128459 A1 | 4/2001 |
| WO | 200149213 A3 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 2008042266 A2 | 4/2008 |
| WO | 08070797 A2 | 6/2008 |
| WO | 2008125153 A1 | 10/2008 |
| WO | 2008138584 A1 | 11/2008 |
| WO | 2008150529 A1 | 12/2008 |
| WO | 2009029199 A1 | 3/2009 |
| WO | 2009042196 A2 | 4/2009 |
| WO | 2009045338 A1 | 4/2009 |
| WO | 2009061389 A2 | 5/2009 |
| WO | 2009091509 A1 | 7/2009 |
| WO | 2009149462 A2 | 12/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012026965 A2 | 3/2012 |
| WO | 2012036741 A2 | 3/2012 |

OTHER PUBLICATIONS

International Search Report Application No. PCT/US2011/048989, dated Dec. 15, 2011.
International Search Report Application No. PCT/US2011/048967, dated Dec. 15, 2011.
International Search Report and Written Opinion for Application No. PCT/US2011/001615 dated Jul. 11, 2012.
Alkhatib, U.S. Appl. No. 13/216,124, filed Aug. 23, 2011, titled "Leaflet Suturing to Commissure Points for Prosthetic Heart Valve".
International Search Report for Application No. PCT/US2011/001597 dated Mar. 7, 2012.
Knippel, U.S. Appl. No. 13/234,782, filed Sep. 16, 2011, titled "Staged Deployment Devices and Method for Transcatheter Heart Valve Delivery".

(56) References Cited

OTHER PUBLICATIONS

Morris, U.S. Appl. No. 13/788,820, filed Mar. 7, 2013, titled "Devices and Methods for Transcatheter Heart Valve Delivery".
Wang, U.S. Appl. No. 13/212,442, filed Aug. 18, 2011, titled "Staged Deployment Devices and Methods for Transcatheter Heart Valve Delivery Systems".
International Search Report for Application No. PCT/US2011/001450 dated Mar. 5, 2012.
Australian Examination Report for Application No. 2011293898 dated Jul. 26, 2013.
International Search Report and Written Opinion for Application No. PCT/US2013/039407 dated Feb. 10, 2014.
International Search Report and Written Opinion for Application No. PCT/US2011/001450 dated Mar. 5, 2012.
Walther et al., "Transapical approach for sutureless stent-fixed aortic valve implantation: experimental results"; European Journal of Cardio-thoracic Surgery 29 (2006) 703-708 (Jan. 30, 2006).
Todd M. Dewey et al., "Transapical aortic valve implantation: an animal feasibility study"; The annals of thoracic surgery 2006; 82: 110-116 (Feb. 13, 2006).
Samuel V. Lichtenstein et al., "Transapical Transcatheter Aortic Valve Implantation in Humans", Circulation. 2006; 114: 591-596 (Jul. 31, 2006).
Christoph H. Huber, et al., "Direct-Access Valve Replacement", Journal of the American College of Cardiology, vol. 46, No. 2, pp. 366-370, (Jul. 19, 2005).
M. J. Mack, "Minimally invasive cardiac surgery", Surgical Endoscopy, 2006, 20:S488-S492, DOI: 10.1007/s00464-006-0110-8 (presented Apr. 24, 2006).
John G. Webb et al., "Percutaneous Aortic Valve Implantation Retrograde From the Femoral Artery", Circulation, 2006; 113:842-850 (Feb. 6, 2006).
Samuel V. Lichtenstein, "Closed heart surgery: Back to the future", The Journal of Thoracic and Cardiovascular Surgery, vol. 131, No. 5, pp. 941-943, May 2006.
Textbook "Transcatheter Valve Repair", 2006, pp. 165-186.
Ruiz, Carlos, Overview of PRE-CE Mark Transcatheter Aortic Valve Technologies, Euro PCR, dated May 25, 2010.
Quaden, Rene, et al., Percutaneous aortic valve replacement: resection before implantation, 836-840,European J. of Cardio-thoracic Surgery, 27 (2005).
Knudsen, L.L., et al., Catheter-implanted prosthetic heart valves, The International Journal of Artificial Organs, vol. 16, No. 5 1993, pp. 253-262.
Moazami, Nader, et al., Transluminal Aortic Valve Placement, Moazami, ASAIO Journal, 1996; 42:M381-M385.
Andersen, Henning Rud, Transluminal Catheter Implanted Prosthetic Heart Valves, International Journal of Angiology 7:102-106 (1998).
Andersen, H. R., et al., Transluminal implantation of artificial heart valves, European Heart Journal (1992) 13, 704-708.
Zegdi, Rachid, MD, PhD et al., Is It Reasonable to Treat All Calcified Stenotic Aortic Valves With a Valved Stent?, 579-584, J. of the American College of Cardiology, vol. 51, No. 5, Feb. 5, 2008.
Braido, et al., U.S. Appl. No. 29/375,243, filed Sep. 20, 2010, titled "Surgical Stent Assembly".
Braido, U.S. Appl. No. 29/375,260, filed Sep. 20, 2010, titled "Forked Ends".
European Search Report for Application No. EP15171169.4 dated Oct. 16, 2015.
Supplementary European Search Report for Application EP11857681.8 dated Nov. 16, 2017.
Pavenik et al., "Aortic and venous valve for percutaneous insertion," Minimally Invasive Therapy & Allied Technologies, 9:3-4 (2000), 287-292.
Martin, Caitlin, Thuy Pham, and Wei Sun, "Significant differences in the material properties between aged human and porcine aortic tissues," European Journal of Cardio-Thoracic Surgery, 40.1 (2011), 28-34.
Sauren, A.A.H.J. et al., "The mechanical properties of porcine aortic valve tissues," Journal of Biomechanics, 16.5 (1983), 327-337.
Gundiah, Namrata et al., "Asymmetric mechanical properties of porcine aortic sinuses," The Annals of Thoracic Surgery, 85.5 (2008), 1631-1638.
Gundiah, Namrata et la., "Significant material property differences between the porcine ascending aorta and aortic sinuses," Journal of Heart Valve Disease, 17.6 (2008), 606-613.
Extended European Search Report and Written Opinion for EP11820608.5 dated Mar. 5, 2018.
European Search Report for Application No. EP 21165142, dated Jul. 8, 2021, 7 pages.

* cited by examiner

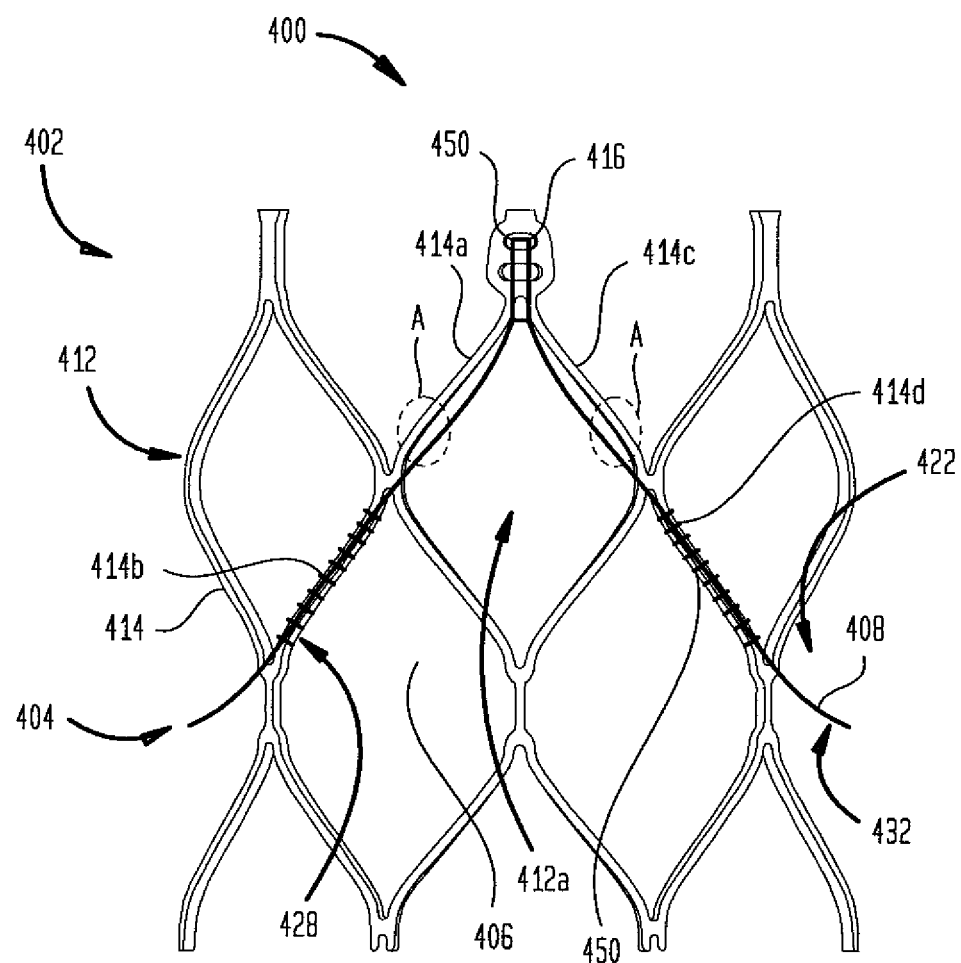

LEAFLET SUTURING TO COMMISSURE POINTS FOR PROSTHETIC HEART VALVE

CROSS-REFERENCE TO RELATED APPLICATIONS

The present application is a continuation of U.S. patent application Ser. No. 15/635,476 filed Jun. 28, 2017, which claims the benefit of the filing date of U.S. Provisional Patent Application No. 61/438,451, filed Feb. 1, 2011, all of which are incorporated herein by reference.

BACKGROUND OF THE INVENTION

The present invention relates to heart valve replacement and, in particular, to collapsible prosthetic heart valves. More particularly, the present invention relates to collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve assembly or structure mounted on a stent. There are many types of stents that may be used. However, two types of stents on which the valve structures are ordinarily mounted include: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implantation site in the patient (e.g., at or near the annulus of the patient's heart valve that is to be replaced by the prosthetic valve), the prosthetic valve can be deployed or released from the delivery apparatus and expanded to the full operating size. For balloon-expandable stents, this generally involves releasing the entire valve, assuring its proper location, and then expanding a balloon positioned within the stent. For self-expanding stents, on the other hand, the stent automatically expands as the sheath covering the valve is withdrawn.

The leaflets in a collapsible prosthetic heart valve, over their useful life, must open and close millions of times. This repeated movement can cause various stresses on the leaflets and, in particular, where they are secured to the rest of the valve. Improper or inadequate attachment can lead to tearing of pulling away from the stent and failure of the valve. And valve failure, in the circulatory system, can have significant consequences for the patient. Accordingly, there remains a need for improved methods of producing heart valves and securing valve leaflets in collapsible prosthetic heart valves.

SUMMARY OF THE INVENTION

The present disclosure relates to prosthetic heart valves. In one embodiment, the prosthetic heart valve includes a stent and a valve assembly. The stent has a collapsed condition and an expanded condition and includes a plurality of commissure points disposed thereon. The valve assembly is secured to the stent and includes a plurality of leaflets. Each leaflet includes a free edge. An end portion of the free edge of the leaflet is folded and sutured to a corresponding one of the plurality of the commissure points.

In an embodiment of the present invention, the end portions of the free edges of first and second adjacent leaflets are sutured to one another. In another embodiment, the prosthetic heart valve further includes a reinforcement layer disposed between the folded end portions of the free edge of the leaflet.

In certain embodiments of the present invention, the folded end portion of the free edge of the leaflet is generally parallel to the immediately adjacent portions of the leaflet and/or generally perpendicular to the commissure point. In other embodiments, the folded end portion of the free edge of the leaflet is generally perpendicular to the immediately adjacent portions of the leaflet and/or generally parallel to the commissure point.

The free end of the folded end portion of the free edge of the leaflet may extend beyond the suture toward the immediately adjacent portion of the leaflet. In yet another embodiment, the end portion of the free edge of the leaflet may be rolled into a generally spiral configuration. In still another embodiment, the folded end portion of the free edge of the leaflet may include two or more folds.

The end portion of the free edge of the leaflet may wrap at least partially around the commissure point. A web overlying the end portion of the free edge of the leaflet may substantially wrap around the commissure point and may be sutured to be end portion and the commissure point.

Moreover, the leaflet may include "tabs" or ends which are attached to the commissure points or a portion of the attached edge may be sutured thereto.

According to yet another embodiment of the present invention, a prosthetic heart valve includes a stent and a valve assembly disposed within the stent. Each of the stent and the valve assembly has a collapsed condition and an expanded condition. The stent has a proximal end and a distal end. A plurality of commissure points is disposed on the stent. The valve assembly includes a plurality of leaflets, each of which has a free edge. An end portion of the free edge of the leaflet is folded and sutured to a corresponding one of the commissure points. The end portion is folded in a configuration selected from the group consisting of a U-shaped pleat, an S-shaped pleat, a generally spiral roll and a U-shaped pleat enveloped by an external web.

BRIEF DESCRIPTION OF THE DRAWINGS

Various embodiments of the present inventions are disclosed herein with reference to the drawings, wherein:

FIG. 3 is a developed view of a portion of a collapsible prosthetic heart valve according to yet another embodiment of the present invention in which some portions of the leaflets of the valve assembly are attached to the stent and disposed substantially along certain stent struts;

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
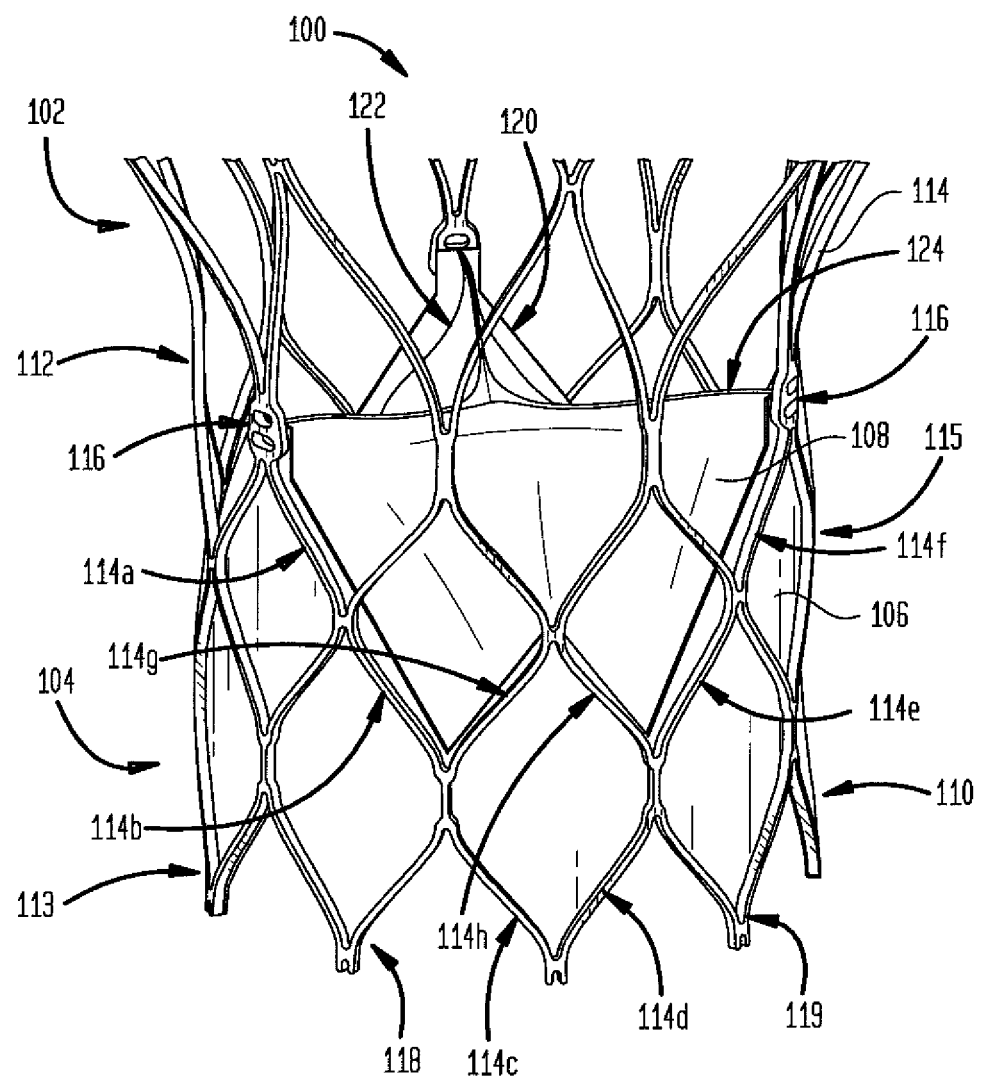
FIG. 1 is a partial side elevational view of a collapsible prosthetic heart valve according to an embodiment of the present invention.

As seen in FIG. 1, a collapsible prosthetic heart valve 100 typically includes a stent or frame 102 supporting a valve assembly 104. Examples of collapsible prosthetic heart valves are described in International Patent Application Publication No. WO/2009/042196; U.S. Pat. Nos. 7,018, 406; 7,329,278, United States Patent Application Publication Nos. 2005/0113910 and 2009/0030511, the disclosures of all of which are hereby incorporated herein by reference.

The prosthetic heart valve 100 is designed to replace the function of a native aortic valve of a patient. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110 and an aortic section (not shown). Each of the annulus section 110 and the aortic section of the stent 102 includes a plurality of cells 112 connected to one another around the stent. The annulus section 110 and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure points 116 connecting at least two cells 112 in the longitudinal direction of the stent 102. The commissure points 116 may include eyelets for facilitating the suturing of a valve assembly 104 to the stent 102.

The prosthetic heart valve 100 also includes a valve assembly 104 attached inside the annulus section 110 of the stent 102. United States Patent Application Publication Nos. 2008/0228264, filed Mar. 12, 2007; 2008/0147179, filed Dec. 19, 2007; 2005/0113910, filed Jul. 10, 2004; and 2009/0030511, filed Jan. 29, 2009, the entire disclosures of all of which are hereby incorporated herein by reference, describe suitable valve assemblies. The valve assembly 104 may be wholly or partly formed of any suitable biological material or polymer materials in the forms of sheets, nonwoven and woven fabrics and the like. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. A first edge 122 of each leaflet 108 may be attached to the stent 102 by any suitable attachment means, such as suturing, stapling, adhesives or the like. A second or free edge 124 of each leaflet 108 may coapt with the corresponding free edges of the other leaflets, thereby enabling the leaflets to function collectively as a one-way valve.

Irrespective of the attachment means employed, the leaflets 108 may be attached to the stent 102 along at least some struts 114 of the stent 102 to enhance the structural integrity of the valve assembly 104. As a consequence of this attachment, the struts 114 help support the leaflets 108 of the valve assembly 104 and may therefore reduce the strain in the leaflets.

As shown in FIG. 1, at least one leaflet 108 may be attached to the stent 102 so that its first edge 122 is disposed substantially along specific struts 114*a*, 114*b*, 114*c*, 114*d*, 114*e* and 114*f* located in the annulus section 110 of the stent. That is, the edge 122 is positioned in substantial alignment with struts 114*a*, 114*b*, 114*c*, 114*d*, 114*e*, and 114*f*. Also as shown, the edge 122 can be roughly parallel to the edge of the cuff 106. However, of course, the cuff 106 need not be cut to follow the slope or pattern of the struts. Struts 114*a*, 114*b*, and 114*c* may be connected to one another in substantially end-to-end fashion diagonally along three cells 112, beginning with an end of the strut 114*a* connected to a commissure point 116 and ending with an end of strut 114*c* connected to an end of strut 114*d*. Struts 114*c* and 114*d* are part of the same cell 112 and may collectively define a substantially right angle between them. Struts 114*d*, 114*e*, and 114*f* may be connected to one another in substantially end-to-end fashion diagonally along three cells 112, beginning with an end of the strut 114*f* connected to a commissure point 116 and ending with the connection between an end of strut 114*c* and an end of strut 114*d*.

As discussed above, the leaflets 108 may be attached directly to and supported by the struts 114*a*, 114*b*, 114*c*, 114*d*, 114*e*, and 114*f*, such as by suturing. In such event, the cuff 106 may perform little or no supportive function for the leaflets 108, and the thickness of the cuff 106 may, therefore, be reduced. Reducing the thickness of the cuff 106 results in a decrease in the volume of the valve assembly 104 in the collapsed condition. This decreased volume is desirable as it enables the prosthetic heart valve 100 to be implanted in a patient using a delivery device that is smaller than conventional delivery devices. In addition, since the material forming the stent 114 is stronger than the material forming the cuff 106, the stent may perform the supportive function for the leaflets 108 better than the cuff.

The volume of the valve assembly 104 may be further reduced by having the cuff 106 cover only a portion of the surface of annulus section 110. With continued reference to FIG. 3, the first or proximal end 118 of the cuff 106 may substantially follow the contour of the first or proximal end 119 of the stent 102. As such, the proximal end of the cuff 106 may have a generally sinusoidal or zigzag shape. This eliminates any free edge of the cuff 106, which otherwise might extend directly between the cusps of the cells 112 at the proximal end 119 of the stent 102, and enables the entire length of the proximal end 118 of the cuff 106 to be secured to the stent 102. The second or distal end 120 of the cuff 106, on the other hand, may be disposed substantially along at least some struts 114, but not necessarily the struts in a single annular row of cells 112.

More particularly, the distal end 120 of the cuff 106 may follow the stent struts 114 up to the commissure points 116, such that the cuff 106 covers all of the cells 112 in the bottom annular row 113 of cells 112 and in a second annular row 115 of cells located between the commissure points and the proximal end 119 of the stent 102, but covers a lesser area of cells in the annular regions between the commissure points. In other words, the distal end 120 of the cuff 106 may be disposed substantially along struts 114a, 114b, 114e, 114f, 114g and 114h, as shown in FIG. 1. Strut 114g may be connected at one end to strut 114h, and at the other end to the intersection of struts 114b and 114c. Strut 114h may be connected at one end to strut 114g, and at the other end to the intersection of struts 114d and 114e. Struts 114c, 114d, 114g, and 114h collectively form a single cell 112.

As a result of the foregoing configuration, all of the cells 112 in the bottom annular row 113 of cells 112 may be entirely covered by the cuff 106. The cuff 106 may also entirely cover those cells 112 in the second annular row 115 that are located directly below the commissure points 116. All of the other cells 112 in the stent 102 may be open or not covered by the cuff 106. Hence, there may be no cells 112 which are only partially covered by the cuff 106.

Since the edges of the valve leaflets 108 extend up to the second annular row 115 of cells 112 only in the regions of the commissure points 116, there is little to no likelihood of leakage in the area of the cells between the commissure points in the second annular row of cells, and therefore no need for the cuff 106 to cover this area. This reduction in the area of the cuff 106, both at the proximal end 118 and at the distal end 120 thereof, reduces the amount of material in the valve assembly 104, thereby enabling the prosthetic valve 100 to achieve a smaller cross-section in the collapsed condition.

Figure 2:
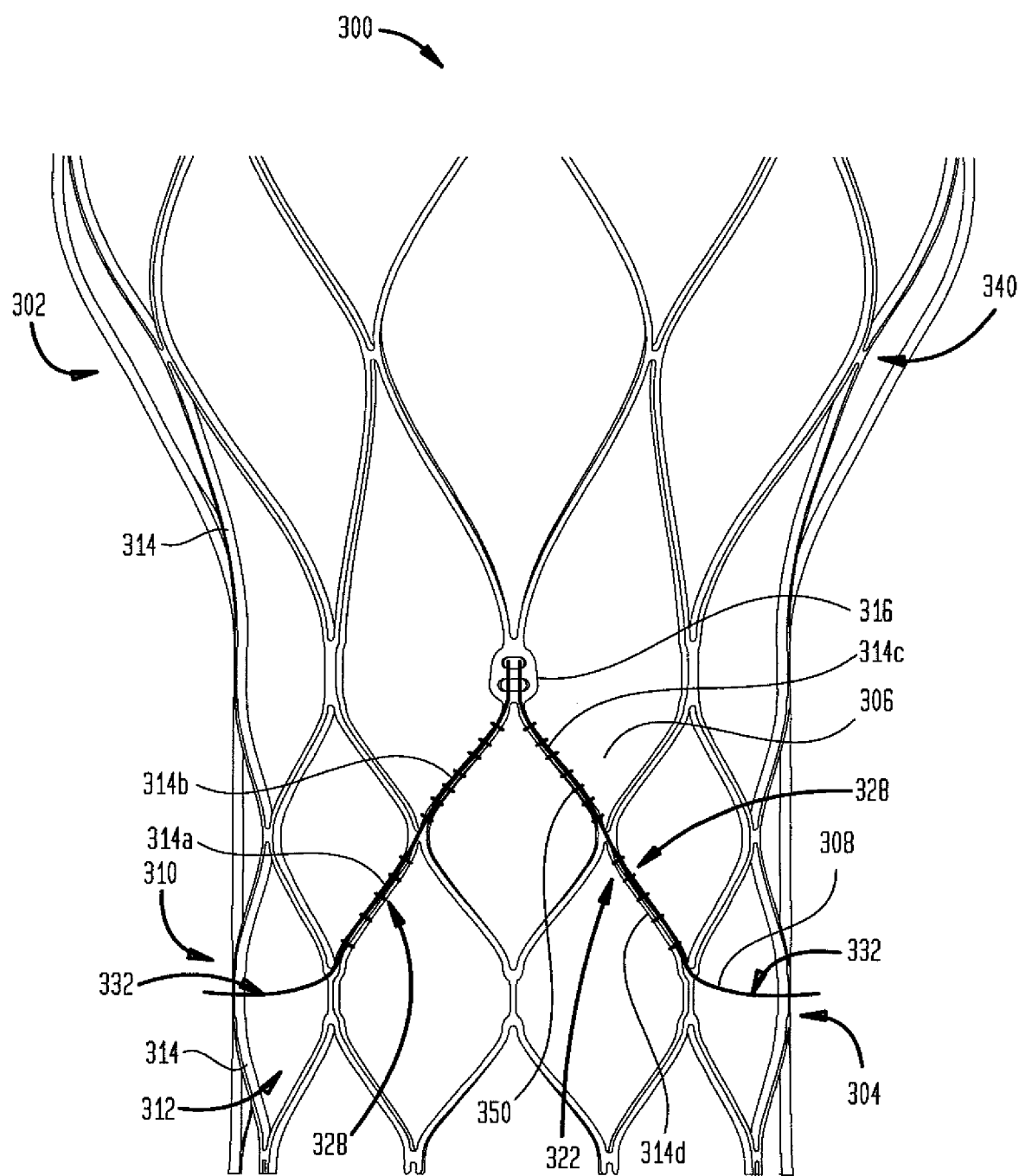
FIG. 2 is a developed view of a portion of a collapsible prosthetic heart valve according to a further embodiment of the present invention in which an edge of the leaflets is disposed substantially along several stent struts.

With reference to FIG. 2, a prosthetic heart valve 300 according to another embodiment of the present invention includes a stent or frame 302, which may be similar to stent 102. The stent 302 may include an aortic section 340 and an annulus section 310. Each of the aortic section 340 and the annulus section 310 may include a plurality of cells 312 connected to one another in one or more annular rows. The cells 312 of the aortic section 340 may be larger than the cells of the annulus section 310. Each cell 312 is formed by a plurality of struts 314. For example, each cell 312 may be formed by four struts 314 and may be substantially diamond-shaped when the stent 302 is in an expanded condition. The stent 302 may further include one or more commissure points 316 for facilitating suturing of a valve assembly 304 to the stent. Each commissure point 316 may interconnect two cells 312 in the same annular row and two cells in different annular rows.

The valve assembly 304 may be attached inside the stent 302, and may include a cuff 306 and a plurality of leaflets 308 which collectively function as a one-way valve. The cuff 306 may be located on the inside surface of the stent 302, on the outside surface of the stent, or on both the inside surface and the outside surface. Each leaflet 308 includes an edge 322 attached to the stent 302 and a second free edge 324. An upper portion 328 of the edge 322 may be attached to the stent 302 so as to be disposed substantially along the path of certain struts 314 that lead to the commissure points 316. For example, an upper portion 328 of the edge 322 of at least one leaflet 308 may be attached to, and disposed substantially along, struts 314a and 314b, and an upper portion 328 of the edge 322 of an adjacent leaflet 308 may be attached to, and disposed substantially along, struts 314c and 314d. As such, struts 314a, 314b, 314c, and 314d help support these adjacent leaflets 308. The upper portions 328 of the edges 322 of adjacent leaflets 308 may be attached to the commissure point 316 and struts 314a, 314b, 314c, and 314d using sutures 350. Struts 314b and 314c may each have one end attached to a commissure point 316 and each may be part of the same cell 312.

Alternatively, struts 314b and 314c may be attached directly to one another. Struts 314a and 314b may be connected in an end-to-end fashion, and may be part of different cells 312 that are adjacent to one another. Similarly, struts 314c and 314d may be connected in an end-to-end fashion, and may be part of different cells 312 that are adjacent to one another.

With reference to FIG. 3, a collapsible prosthetic heart valve 400 according to an embodiment of the present invention includes a stent 402, which may be similar to stent 102. The stent 402 has collapsed and expanded conditions and includes a plurality of cells 412 connected to one another in annular rows around the stent 402. Each cell 412 is formed by a plurality of struts 414 and may be substantially diamond shaped when the stent 402 is in the expanded condition. For example, one cell 412 may be formed by four interconnected struts 414.

The stent 402 may further include one or more commissure points 416 that interconnect two adjacent cells 412 located in one annular row and two other cells 412 located in the next adjacent rows above and below the one row. The commissure points 416 may facilitate the suturing of a valve assembly 404 to the stent 402.

The valve assembly 404 may include a cuff 406 attached to the interior and/or exterior of the stent 402. In addition to the cuff 406, the valve assembly 404 includes a plurality of leaflets 408 attached to the stent 402 and collectively defining a one-way valve. Each leaflet 408 includes a first edge 422 attached to the stent 402 and a second free edge 424. At least one leaflet 408 may be attached to the stent 402 so that the upper portions 428 of its edge 422 are substantially disposed along the path of certain struts 414.

As shown in FIG. 3, one upper portion 428 of the edge 422 of one leaflet 408 may be connected to a commissure point 416 and may be disposed along and connected to a strut 414b spaced from the commissure point. A section A of the upper portion 428 of the edge 422 may follow a substantially direct path between the commissure point 416 and an end of stent strut 414b. Similarly, one upper portion 428 of the edge 422 of another leaflet 408 may be connected to the commissure point 416 and may be disposed along and connected to a strut 414d spaced from the commissure point. A section A of the upper portion 428 of the edge 422 of this second leaflet 408 may follow a substantially direct path between the commissure point 416 and an end of stent strut 414d. The edges 422 of the leaflets 408 may be connected to the commissure point 416 and to the struts 414b and 414d using sutures.

In operation, any of the embodiments of the prosthetic heart valve described above may be used to replace a native heart valve, such as the aortic valve. The prosthetic heart valve may be delivered to the desired site (e.g., near a native valve annulus) using any suitable delivery device known in the art. During delivery, the prosthetic heart valve is disposed inside the delivery device in the collapsed condition. The delivery device may be introduced into a patient using the transfemoral, transapical or transseptal approach. Once the delivery device has reached the target site, the user may deploy any of the prosthetic heart valves described above. Upon deployment, the prosthetic heart valve expands into secure engagement within the native valve annulus. When the prosthetic heart valve is properly positioned inside the heart, it works as a one-way valve, allowing blood to flow in one direction and preventing blood from flowing in the opposite direction.

In each of the prosthetic heart valve embodiments described above, the valve assembly preferably is spaced from the distal or aortic end of the stent by a distance that enables deployment of the heart valve by an amount sufficient for the valve leaflets of the prosthetic valve to operate as intended, while the distal end of the stent remains captured by the delivery device. More particularly, the annulus end of the prosthetic heart valve may be deployed first while the aortic end of the prosthetic heart valve remains at least partially covered by the distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly.

If the user determines that the positioning and operation of the valve are acceptable, the remainder of the valve may be deployed. However, if it is determined that the leaflet position is improper or that the valve is not functioning properly, the user may resheath the valve and either reposition it for redeployment, or remove it entirely from the patient. This can be particularly important in very high risk patients who would typically be recipients of these types of valves, because of the nature of their condition and the impact that may have on the shape and/or condition of the native valve and valve annulus. Of course, the prosthetic heart valve of the present invention can be delivered by deploying the aortic or distal end first as well.

Anatomical irregularities at the implantation site can create issues with respect to the proper functioning and wear of the prosthetic heart valve. Another aspect of the invention is the achievement of a better functioning valve in the various shapes, such as elliptical, round, irregular, etc., that the valve may assume upon implantation and use. This may depend, in some instances, not only on leaflet positioning, commissure positioning, and valve geometry, as previously described, but also can relate to the manner in which the leaflets are attached to the valve assembly, the stent, and in particular, the commissure attachment points. As the stent is deformed by implantation and use, if leaflet positioning and geometry are not correct, undesirable load forces at the leaflet edges, particularly at the commissure attachment points, can be created. This can lead to tearing of the leaflets and/or cuff and eventually valve failure.

Some arrangements that are intended to minimize valve failure and promote better valve function are illustrated in FIGS. 4A-4I. FIGS. 4A-4I show various arrangements for attaching the leaflets to the commissure points 116 in order to promote better and longer valve function. Which particular arrangement is used may depend, inter alia, on the type of valve material used, the thickness of the stent, the dimensions of the commissure points, the type, thickness and placement of the cuff, if any, the overall shape of the valve and valve assembly, and the like. Note that in the various illustrations which represent the end views, as seen from the distal end of the stent along the longitudinal axis of the stent toward the proximal end of the stent, of a commissure point and the attachment of the leaflets thereto (in which the dashed lines represent suture lines), the cuff is not illustrated for purposes of clarity.

Figure 4A:
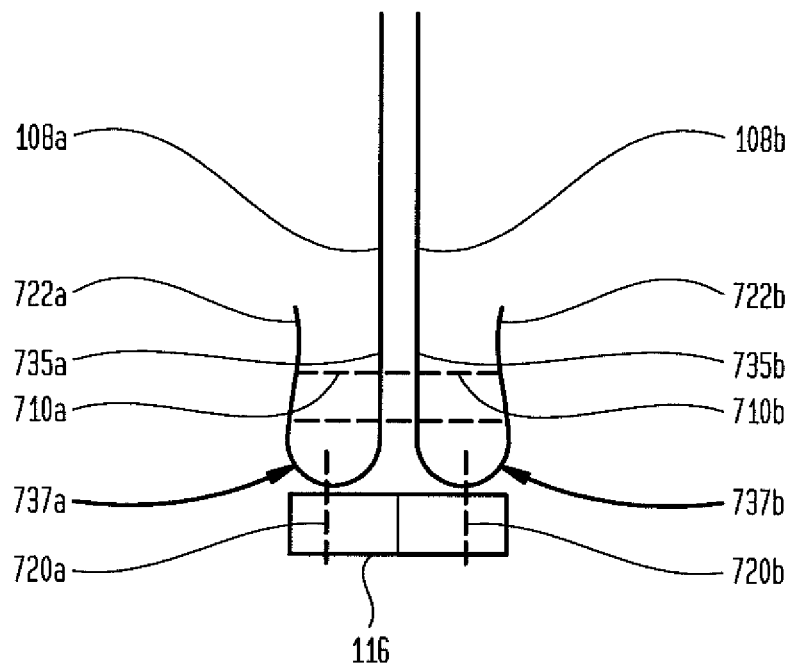
FIGS. 4A-4I are highly schematic end views showing various embodiments of leaflet suturing to a commissure point of the stent according to aspects of the present invention.

Referring to FIG. 4A, portions of two adjacent leaflets 108a and 108b are illustrated. Note that the leaflets 108a and 108b are illustrated as generally parallel to each other only for the sake of simplicity. In actuality, the adjacent leaflets 108a, 108b will generally diverge from one another as they extend away from the commissure point 116. In the illustrated embodiment, an end portion 722a of leaflet 108a is folded in a generally "U-shaped" pleat 737a. Likewise, an end portion 722b of leaflet 108b is folded in a generally "U-shaped" pleat 737b. The folded end portions 722a, 722b may be generally parallel to the immediate adjacent portions 735a, 735b, respectively, of the leaflets 108a, 108b and generally perpendicular to the commissure point 116. The folded end portions 722a, 722b may be sutured to one another by one or more sutures 710 (a pair of sutures illustrated). In addition, end portion 722a may be sutured to commissure point 116 via one or more sutures 720a and end portion 722b may be sutured to commissure point 116 via one or more sutures 720b (a single suture illustrated). Since the sutures 710a, 710b pass through the U-shaped pleats 737a, 737b, respectively, the stresses induced in the leaflet 108a, 108b due to the sutures at the sites of the sutures may be more widely distributed, thereby minimizing the likelihood of a tear in the leaflets due to suturing.

Figure 4B:
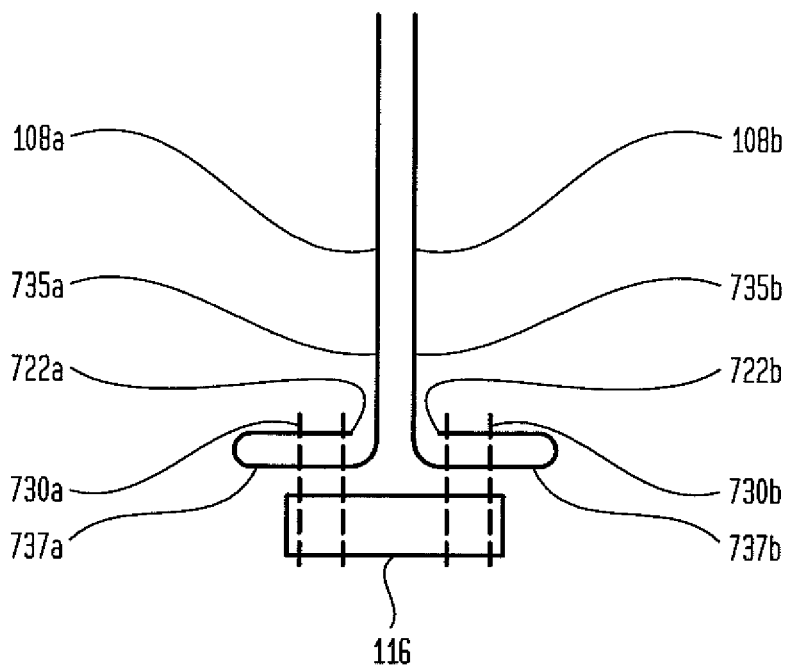

FIG. 4B illustrates the suturing of the leaflets to the commissure point 116 according to another embodiment of the invention. Each of the end portions 722a, 722b of the respective leaflets 108a, 108b is folded in a generally "U-shaped" pleat 737a, 737b, respectively, as in the embodiment of FIG. 4A, and the U-shaped pleats 737a, 737b are then bent outwardly so as to lie substantially perpendicular to the immediate adjacent portions 735a, 735b of the leaflets 108a, 108b and generally parallel to the commissure point 116. The U-shaped pleat 737a may be sutured to the commissure point 116 via one or more sutures 730a. Similarly, the U-shaped pleat 737b may be sutured to the commissure point 116 via one or more sutures 730b. In variants hereof, less than or more than two sutures may be employed to suture each folded end portion 722a, 722b to the commissure point 116. Since sutures 730a, 730b pass through the U-shaped pleats 737a, 737b, respectively, the stresses induced in the leaflets 108a, 108b at the sites of the sutures may be more widely distributed, thereby minimizing the likelihood of a tear in the leaflets due to suturing.

Figure 4C:
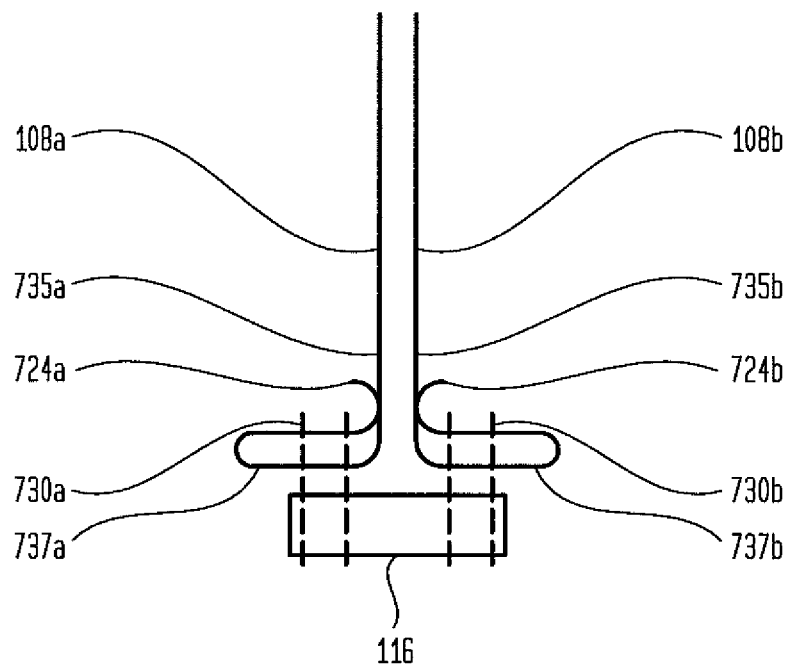

FIG. 4C illustrates a variant of the embodiment of FIG. 4B. In the embodiment of FIG. 4C, the end portions 722a, 722b have much larger unsutured free edges 724a, 724b, respectively, which extend toward the immediate adjacent portions 735a, 735b of the leaflets 108a, 108b, respectively, and then curl back toward the U-shaped pleats 737a, 737b, respectively. This configuration reduces the possibility of tearing the free edges 724a, 724b of end portions 722a, 722b due to the stress induced by the suturing.

Figure 4D:
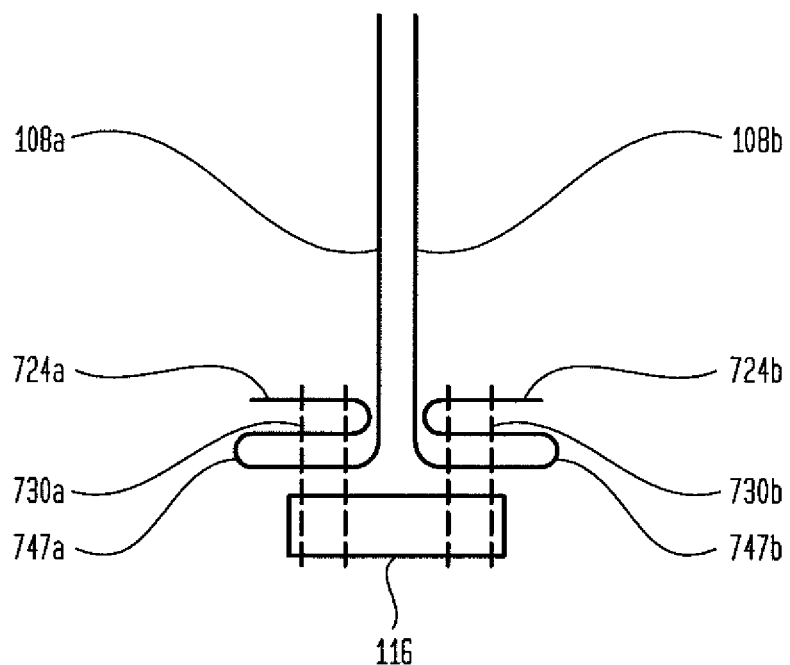

Referring to FIG. 4D, the embodiment illustrated is generally similar to the embodiments of FIGS. 4B and 4C. Whereas in the embodiments of FIGS. 4B and 4C, the end portions 722a, 722b of the leaflets 108a, 108b have a single fold in the form of U-shaped pleats 737a, 737b, respectively, the end portions 722a, 722b in the embodiment of FIG. 4D include multiple folds in a generally compressed "S-shaped" pleat or a Heintz pleat 747a, 747b, respectively. While two such folds are shown in FIG. 4D for the pleats 747a, 747b, it will be understood that pleats 747a, 747b may include more than two such folds. The additional folds in the embodiment of FIG. 4D further distribute the stresses due to suturing and reduce the likelihood of tearing the leaflets 108a and 108b.

Figure 4E:
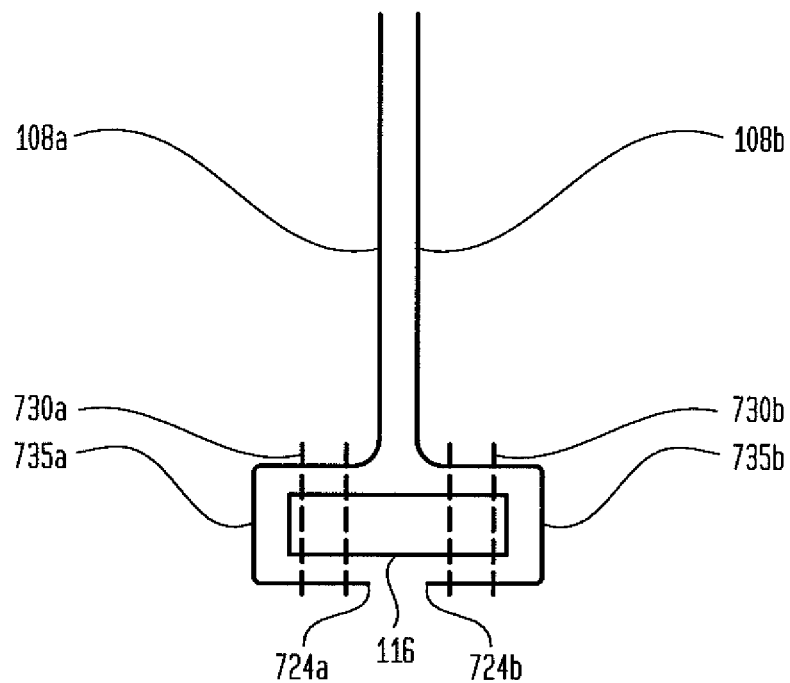

Now referring to FIG. 4E, leaflets 108a, 108b are sutured to the commissure point 116 according to another embodiment of the invention. The end portion 722a of leaflet 108a is wrapped around one side of commissure point 116 such that a U-shaped pleat 735a is formed, which generally envelopes one side of the commissure point. Likewise, the end portion 722b of leaflet 108b is wrapped around the other side of commissure point 116 such that a U-shaped pleat 735b is formed, which generally envelopes the other side of the commissure point. Thus, the commissure point 116 may be enveloped on opposing sides by the end portions 722a and 722b, respectively. One or more sutures 730a (one pair of suture illustrated) attach the end portion 722a to the commissure point 116, and one or more sutures 730b (one pair of suture illustrated) attach the end portion 722b to the commissure point 116. The suturing sites on the end portions 724a and 724b are situated further apart due to the presence of the commissure point 116, thereby reducing the stress due to suturing in the leaflets 108a and 108b. Note that this type of arrangement might necessitate some change in how and where the cuff 106 is attached. It could be attached on the ablumenal surface over the free ends 724a, 724b. In other configurations, the cuff 106 could also be split in the proximity of the commissure point 116 so that either end may be attached over the top of the inner portion of the folds.

The cuff 106 could also be attached to the lumenal surface but disposed between and under the commissure points and the proximal end of the stent. These types of cuff arrangements may also be used in connection with, for example, the embodiments illustrated in FIGS. 4F and 4G.

Figure 4F:
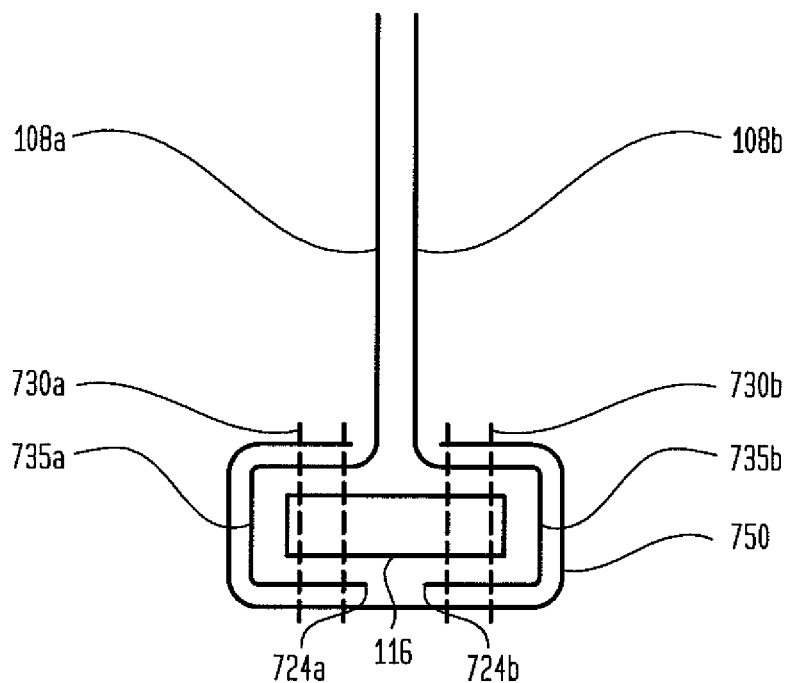

FIG. 4F illustrates an embodiment which generally includes the features of the embodiment illustrated in FIG. 4E. In particular, the end portion 722a of the leaflet 108a is wrapped around one side of commissure point 116 such that a U-shaped pleat 735a is formed which envelopes one side of the commissure point 116. The end portion 722b of the leaflet 108b is wrapped around the other side of the commissure point such that a U-shaped pleat 735b is formed which envelopes the other side of the commissure point 116. A tissue or fabric web 750 is then wrapped around the end portions 722a, 722b and the commissure point 116 from the outside surface (the bottom as seen in FIG. 4F) so as to cover any gap between the free ends 724a and 724b. One or more sutures 730a, 730b (one pair of sutures illustrated for each leaflet 108a, 108b) may attach the web 750 and the end portions 722a, 722b to the commissure point 116. In an exemplary configuration, the web 750 may be formed from any suitable biological material or polymer. Examples of biological materials suitable for the web 750 include, but are not limited to, porcine or bovine pericardial tissue. Examples of polymers suitable for the web 750 include, but are not limited to, polyurethane and polyester. The web 750 provides reinforcement to the end portions 722a, 722b and reduces the stress induced therein due to the suturing.

Figure 4G:
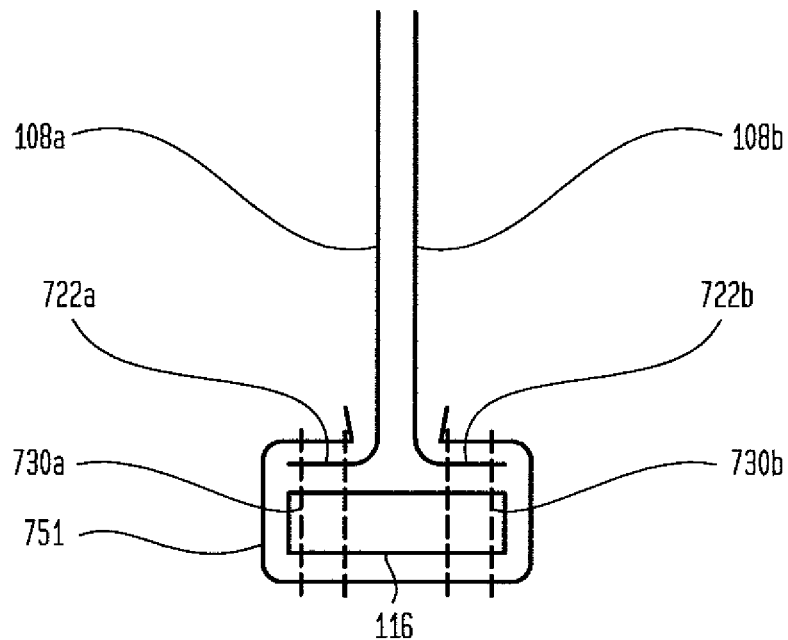

In yet another embodiment illustrated in FIG. 4G, which is a variation of the embodiment illustrated in FIG. 4F, the end portions 722a, 722b of the respective leaflets 108a, 108b generally overlie the commissure point 116 in an L-shaped fold, but do not wrap around the same. A fabric or tissue web 751 is then wrapped around the commissure point 116 so as to overlie the end portions 722a, 722b of the leaflets 108a, 108b. In an exemplary embodiment, the web 751 may be formed from the same materials as may be used for forming the web 750. One or more sutures 730a (one pair of sutures illustrated) may attach the web 751 and the end portion 722a to the commissure point 116. Likewise, one or more sutures 730b (one pair of sutures illustrated) may attach the web 751 and the end portion 722b to the commissure point 116. The web 751 provides reinforcement to the end portions 722a, 722b and reduces the stress induced therein due to the suturing.

Figure 4H:
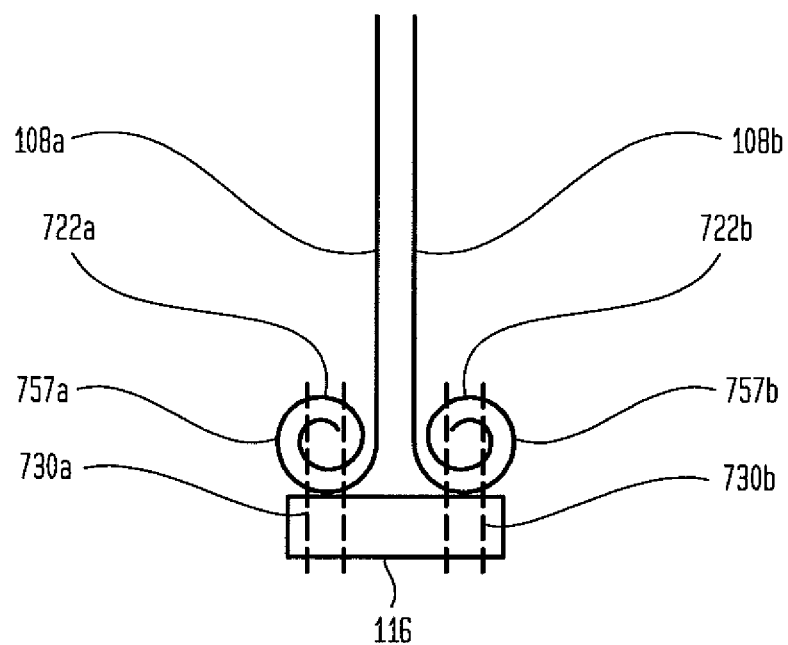

Referring now to FIG. 4H, leaflets 108a, 108b are sutured to the commissure point 116 according to yet another embodiment of the invention. The end portions 722a, 722b of the respective leaflets 108a, 108b are rolled into a generally spiral configuration 757a, 757b, respectively. The rolled end portions 722a, 722b may be sutured to the commissure point 116 via one or more sutures 730a, 730b, respectively. An advantage of the rolled end portions 722a, 722b is that the stresses caused by the sutures 730a, 730b are evenly distributed over the end portions 722a, 722b.

Figure 4I:
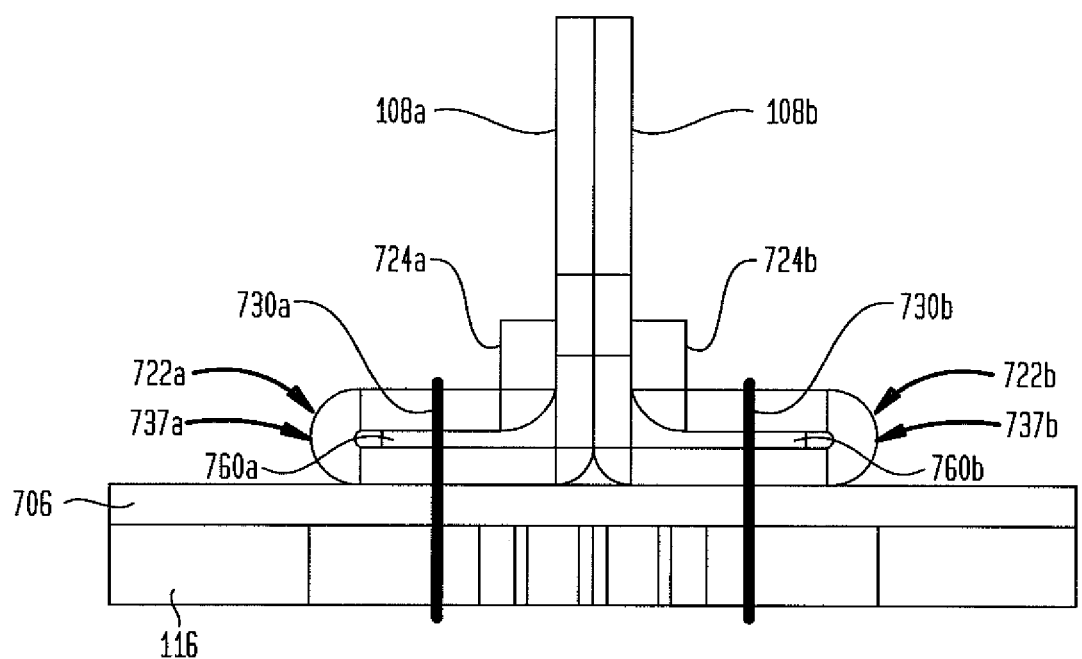

FIG. 4I illustrates another exemplary embodiment of the invention. Each of the end portions 722a, 722b of the respective leaflets 108a, 108b is folded into a generally "U-shaped" pleat 737a, 737b, respectively. A cuff 706 is interposed between the U-shaped pleats 737a, 737b and the commissure point 116. The free ends 724a, 724b of the respective end portions 722a, 722b are attached to respective remainder portions of the leaflets 108a, 108b. Reinforcement tissue or fabric webs 760a, 760b are disposed, respectively, between the folds of each of the end portions 722a, 722b. The webs 760a, 760b may be formed from the same biological or polymeric materials as may be used for forming the web 750. One or more sutures 730a attach the folded end portion 722a along with the web 760a and the cuff 706 to the commissure point 116, while one or more sutures 730b attach the folded end portion 722b along with the web 760b and the cuff 706 to the commissure point. The webs 760a, 760b reinforce the folded portions 722a, 722b.

Figure 5A:
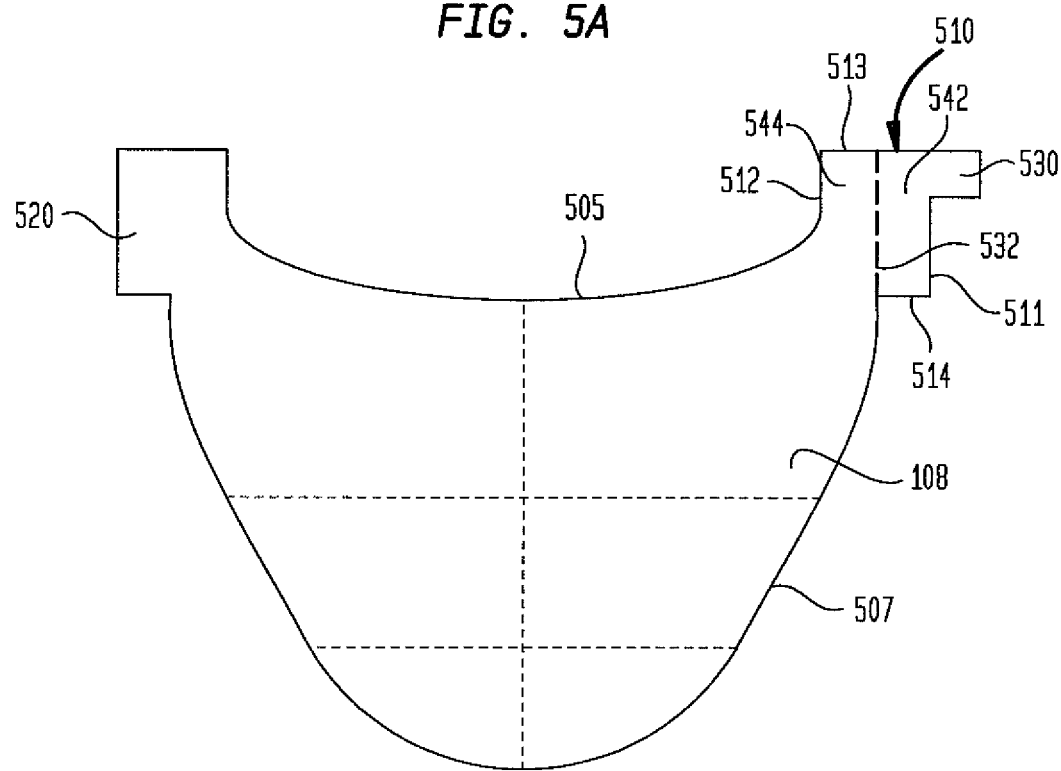
FIGS. 5A-5B are highly schematic front elevational views of two embodiments of the leaflets according to aspects of the present invention.

FIG. 5A schematically illustrates the leaflet 108, which may be sutured to the commissure point 116 of the stent 102 using any of the configurations described above. Leaflet 108 has a free edge 505 and an arcuate edge 507 attached, for example, to one or more struts 114 of the stent 102 as described above. Leaflet 108 may include a generally rectangular tab 510 at one end of the free edge 505 and another generally rectangular tab 520 at the other end of the free edge 505. The tab 510 may be defined by a substantially straight outside edge 511, a substantially straight inside edge 512, that is substantially parallel to the edge 511, a substantially straight top edge 513, and a substantially straight bottom edge 514, that is substantially parallel to the top edge 513 and substantially orthogonal to the edges 511 and 512. The tab 510 may include a further projection 530 projecting laterally from the outside edge 511. The tab 520 may be substantially the same the tab 510, but may omit the further projection 530.

As noted, the leaflet 108 may be attached to the commissure point 116 of the stent 102 using any of the configurations previously described. The following will describe the attachment of the leaflet 108 to the commissure point 116 using the configuration of FIG. 4I. The tab 510 may include an imaginary fold line 532, which is generally aligned with the arcuate edge 507 of the leaflet 108, and is substantially parallel to the edges 511 and 512, dividing the tab 510 into a first portion 542 and a second portion 544. The tab 510 may be folded along the fold line 532 to form, for example, the generally "U-shaped" pleat 737a shown in FIG. 4I.

Figure 5B:
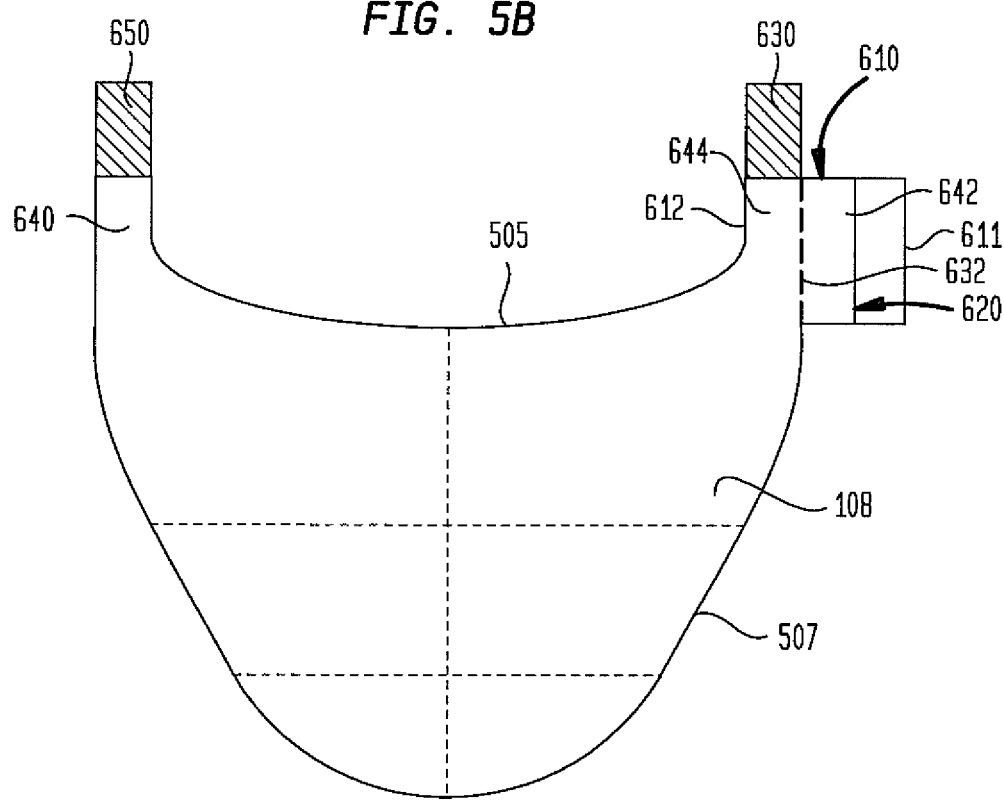
Figure 5C:
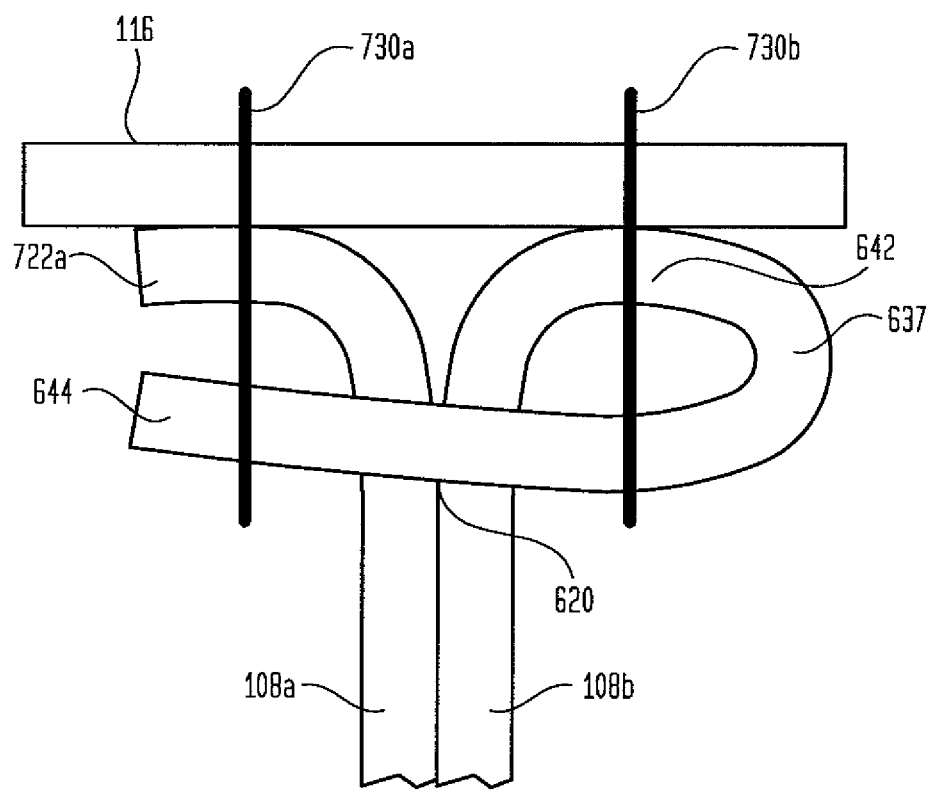
FIG. 5C is a highly schematic end view showing an embodiment of leaflet suturing to a commissure point according to an aspect of the present invention.

FIGS. 5B and 5C illustrate yet another embodiment of the leaflet 108 and the suturing of the leaflet to the commissure point 116. The leaflet 108 may be generally similar to the leaflet 108 of FIG. 5A, except for the differences set forth below. The leaflet 108 may include a generally rectangular tab 610, similar in configuration to the tab 510 of FIG. 5A, extending from one end of the free edge 505, and a similar generally rectangular tab 640 extending from the other end of the free edge 505. Rather than having a further projection extending from the outside edge as with tab 510, however the tab 610 may optionally have a further projection 630 extending from the top edge 613. A similar further projection 650 may extend from the top edge of the tab 640.

As noted, the leaflet 108 may be attached to the commissure point 116 of the stent 102 using any of the configurations previously described. Yet another configuration for attaching the leaflet 108 to the commissure point 116 is shown in FIG. 5C. The tab 610 may include an imaginary fold line 632, which is generally aligned with the arcuate edge 507 of the leaflet 108 and one edge of further projection 630, and is substantially parallel to the outside edge 611 and the inside edge 612 of tab 610, dividing the tab 610 into a first portion 642 and a second portion 644. A generally vertical slit 620, as seen in FIG. 5B, is defined in the first portion 642 of the tab 610 and is substantially parallel to the edges 611 and 612. The tab 610 may be folded along the fold line 632 to form a generally "U-shaped" pleat 637 which extends across leaflets 108a, 108b. The slit 620 accommodates portions of the free edges of the leaflets 108a, 108b. One or more sutures 730a attach the folded second portion 644 of the leaflet 108b and the free end 722a of the leaflet 108a to the commissure point 116. One or more sutures 730b attach the U-shaped pleat 637 to the commissure point 116. Where the tab 610 includes further projection 630, the further projection may be tacked to the stent and then later removed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
   a collapsible and expandable stent having a proximal end, a distal end, a plurality of struts and a plurality of cells defined by the plurality of struts;
   a plurality of commissure points disposed on the stent, each of the commissure points having an inner surface, an outer surface, a first lateral side and a second lateral side, each of the commissure points interconnecting first and second adjacent cells in an annular row of the stent such that the first lateral side faces the first cell and the second lateral side faces the second cell; and
   a collapsible and expandable valve assembly disposed within the stent, the valve assembly including a plurality of leaflets, each of the leaflets having an end portion and a remaining portion, the end portion including a first segment extending from the remaining portion of the leaflet, a terminal portion, and an intermediate portion between the first segment and the terminal portion, the end portion of a first one of the leaflets being folded in a U-shape so that the terminal portion of the first leaflet contacts the first segment of the first leaflet and is attached directly to the first segment of the first leaflet, the end portion of the first leaflet being attached to one of the commissure points in contact with the inner surface of the one commissure point,
   wherein the terminal portion of the first leaflet is oriented generally parallel to the inner surface of the one commissure point.

2. The prosthetic heart valve according to claim 1, wherein the end portion of a second one of the leaflets adjacent the first leaflet is folded in a U-shape so that the terminal portion of the second leaflet contacts the first segment of the second leaflet and is attached directly to the first segment of the second leaflet, the end portion of the second leaflet being attached to the one commissure point in contact with the inner surface of the one commissure point.

3. The prosthetic heart valve according to claim 2, wherein the terminal portion of the second leaflet is oriented generally parallel to the inner surface of the one commissure point.

4. The prosthetic heart valve according to claim 3, wherein the terminal portion of the first leaflet and the first segment of the first leaflet are sutured to the one commissure point.

5. The prosthetic heart valve according to claim 2, further comprising a first suture passing through the terminal portion of the first leaflet, the first segment of the first leaflet and the one commissure point; and
   a second suture passing through the terminal portion of the second leaflet, the first segment of the second leaflet and the one commissure point.

\* \* \* \* \*